United States Patent
Reichelsheimer

(10) Patent No.: US 8,816,295 B2
(45) Date of Patent: Aug. 26, 2014

(54) ADHESIVE DETECTION SYSTEM FOR MAILPIECE CREATION SYSTEM

(71) Applicant: Pitney Bowes Inc., Stamford, CT (US)

(72) Inventor: Jay Reichelsheimer, Shelton, CT (US)

(73) Assignee: Pitney Bowes Inc., Stamford, CT (US)

( * ) Notice: Subject to any disclaimer, the term of this patent is extended or adjusted under 35 U.S.C. 154(b) by 190 days.

(21) Appl. No.: 13/646,208

(22) Filed: Oct. 5, 2012

(65) Prior Publication Data

US 2014/0097350 A1 Apr. 10, 2014

(51) Int. Cl.
| | | |
|---|---|---|
| G01J 1/42 | (2006.01) | |
| G01N 21/84 | (2006.01) | |
| G01N 21/47 | (2006.01) | |
| G01N 21/64 | (2006.01) | |
| B32B 37/12 | (2006.01) | |
| G01N 21/33 | (2006.01) | |

(52) U.S. Cl.
CPC ............ *G01N 21/47* (2013.01); *G01N 21/8422* (2013.01); *G01N 21/64* (2013.01); *B32B 37/1284* (2013.01); *G01N 2021/8427* (2013.01); *G01N 21/33* (2013.01)
USPC ....................................... 250/372

(58) Field of Classification Search
CPC ................................ G01N 21/33; G01N 21/64
USPC ....................................... 250/372
See application file for complete search history.

(56) References Cited

U.S. PATENT DOCUMENTS

| | | | | |
|---|---|---|---|---|
| 4,778,999 A | * | 10/1988 | Fisher | 250/461.1 |
| 5,030,833 A | | 7/1991 | Nozaka et al. | |
| 5,073,951 A | * | 12/1991 | Hayashi | 382/141 |
| 5,493,123 A | | 2/1996 | Knollenberg et al. | |
| 2010/0304008 A1 | | 12/2010 | Lauria et al. | |

FOREIGN PATENT DOCUMENTS

| | | |
|---|---|---|
| EP | 0256742 A3 | 2/1988 |
| EP | 1146330 A3 | 10/2001 |
| EP | 2570260 A1 | 3/2013 |

OTHER PUBLICATIONS

Shur, M.S. et al. "Deep- Ultraviolet Light -Emitting Diodes". IEEE Transactions on Electron Devices IEEE Service Center, Pisacataway , NJ. vol. 57, No. 1. Jan. 1, 2010. pp. 12-25.

* cited by examiner

Primary Examiner — Kiho Kim
(74) Attorney, Agent, or Firm — Michael J. Cummings; Charles R. Malandra, Jr.; Steven J. Shapiro

(57) ABSTRACT

A system and method for detecting adhesive used to produce an envelope in a mailpiece creation system. The system includes a source of ElectroMagnetic (EM) energy in at least the short UV range to illuminate a surface of the substrate material anticipated to have an adhesive deposited thereon in select regions, an EM energy detection device operative to detect energy reflected from the surface of the substrate material in the visible light range and produce a response indicative of the optical absorbance of EM energy in the short UV range; and a processor operative to analyze the response of the EM energy detection device to determine whether light energy in the visible range is below a threshold level to indicate the presence of adhesive deposited on the substrate material.

12 Claims, 4 Drawing Sheets

ADHESIVE DETECTION SYSTEM FOR MAILPIECE CREATION SYSTEM

TECHNICAL FIELD

The present invention relates to mailpiece creation systems, and, more particularly, to a new and useful system and method for detecting an adhesive material on a substrate for use in a mailpiece creation system.

BACKGROUND OF THE INVENTION

Mailpiece creation systems such as mailpiece inserters and mailpiece wrappers are typically used by organizations such as banks, insurance companies, and utility companies to periodically produce a large volume of mail, e.g., monthly billing or shareholders income/dividend statements. In many respects, mailpiece inserters are analogous to automated assembly equipment inasmuch as sheets, inserts and envelopes are conveyed along a feed path and assembled in, or at, various modules of the mailpiece inserter. That is, the various modules work cooperatively to process the sheets until a finished mailpiece is produced.

Mailpiece inserters include a variety of apparatus/modules for conveying and processing a substrate/sheet material along the feed path. Commonly mailpiece inserters include apparatus/modules for (i) feeding and singulating printed content in a "feeder module", (ii) accumulating the content to form a multi-sheet collation in an "accumulator", (iii) folding the content to produce a variety of fold configurations such as a C-fold, Z-fold, bi-fold and gate fold, in a "folder", (iv) feeding mailpiece inserts such as coupons, brochures, and pamphlets, in combination with the content, in a "chassis module" (v) inserting the folded/unfold and/or nested content into an envelope in an "envelope inserter", (vi) sealing the filled envelope in "sealing module" and (vii) printing recipient/return addresses and/or postage indicia on the face of the mailpiece envelope at a "print station".

In lieu of modules for inserting and/or sealing the content material into an "envelope", some mailpiece creation systems employ a wrapping system operative to encapsulate the mailpiece content in an outer wrapping material or substrate. Therein, the content material is fed into a substrate/wrap having a pressure-activated adhesive deposited thereon to enclose/seal the content material in a tubular-shaped envelope wrap. More specifically, the content material is fed into a wrapping module which receives a supply of substrate material from a web of rolled material. Before being fed to the wrapping module, an adhesive application module deposits a polymeric adhesive in a predefined two-dimensional pattern on the substrate material. As the substrate material is folded by the wrapping system, an envelope pocket is produced for receipt of the content material.

More specifically, the supply of substrate material is fed from beneath the deck of the wrapping module and turned downstream to define an open-end for accepting a supply of content material. As the substrate and content material is pulled downstream, a one or more guides fold the substrate material inwardly such that the outboard edge portions overlap. Furthermore, a tube-shaped wrap is produced around the content material as the substrate material is drawn together downstream of the open end. The content-filled tubular structure then is passed under a series of pressure rollers to cause the pressure-activated adhesive to form a series of individual pockets having content material in each. Thereafter, the wrapping module includes a cutting roller to separate the content-filled pockets into separate envelopes.

To obtain the throughput advantages of a mailpiece creation system, and especially one employing a wrapping system, it is important to minimize the downtime of the fabrication system. While a variety of mailpiece fabrication errors can occur to adversely impact throughput, one of the more frequent sources originates from the application of adhesive, or lack thereof, onto the wrapping material substrate. For example, when the supply of adhesive in the adhesive-application module is depleted or does not properly flow, the mailpiece creation system must be stopped/discontinued until a new supply of adhesive is provided, or until the malfunction is corrected.

With respect to the latter, it is not uncommon for one or more glue-heads to malfunction, i.e., becoming clogged thereby stopping the flow of adhesive onto the substrate material. As a consequence, visual inspections must be routinely performed to ensure that the adhesive is properly deposited on the substrate, i.e., thoroughly and evenly. While such visual inspections add a level of redundancy with respect to the application of adhesive, such inspections are difficult due to the optical transparency of the adhesive on the substrate material. Furthermore, while it is known to incorporate additives into the adhesive which can be detected by sensing equipment, such additives are costly and can adversely impact the aesthetic appearance of the mailpiece.

A need, therefore, exists for a system and method for detecting adhesive on a substrate material which does not degrade performance, is cost-effective, and does not adversely impact the aesthetic appearance of a finished mailpiece.

SUMMARY OF THE INVENTION

A system and method for detecting adhesive used to produce an envelope in a mailpiece creation system. The system includes a source of ElectroMagnetic (EM) energy in at least the short UV range to illuminate a surface of the substrate material anticipated to have an adhesive deposited thereon in select regions, an EM energy detection device operative to detect energy reflected from the surface of the substrate material in the visible light range and produce a response indicative of the optical absorbance of EM energy in the short UV range; and a processor operative to analyze the response of the EM energy detection device to determine whether light energy in the visible range is below a threshold level to indicate the presence of adhesive deposited on the substrate material.

BRIEF DESCRIPTION OF THE DRAWINGS

The accompanying drawings illustrate presently preferred embodiments of the invention and, together with the general description given above and the detailed description given below serve to explain the principles of the invention. As shown throughout the drawings, like reference numerals designate like or corresponding parts.

DETAILED DESCRIPTION OF THE INVENTION

The present invention is directed to a system and method for detecting adhesive on a substrate material for use in a mailpiece creation system. While the invention is described in the context of a paper-based wrapping system, i.e., a system which is fed by a paper web, for creating finished mailpieces, the invention is equally applicable to other mailpiece creation systems wherein adhesive is applied to a substrate material used to produce an envelope. Consequently, the detailed description and illustrations are merely indicative of an embodiment of the invention, and, accordingly, the invention should be broadly interpreted in accordance with the appended claims.

Figure 1:
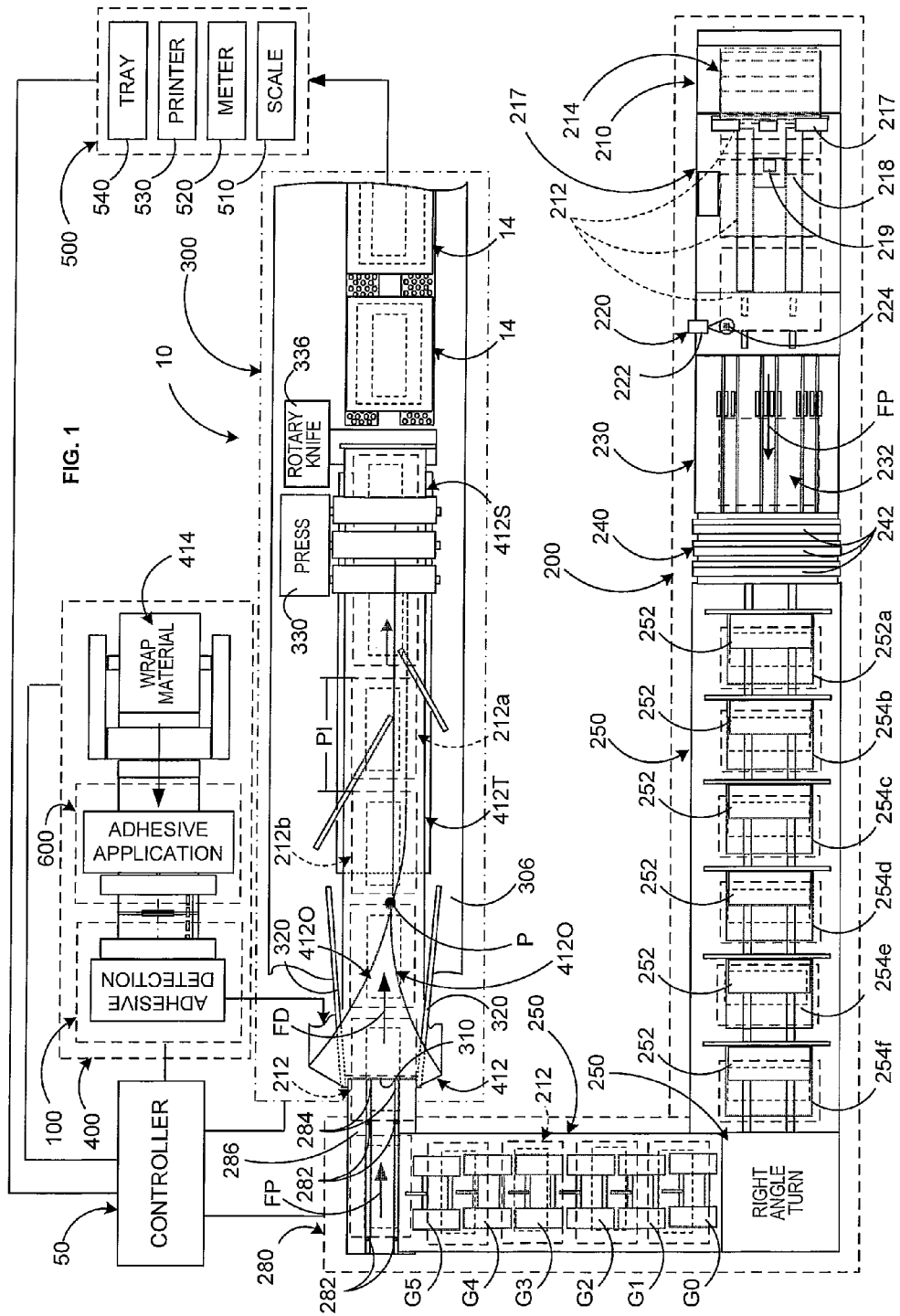
FIG. 1 is a schematic top view of a mailpiece creation system including a system for detecting an adhesive deposited on a substrate material according to the present invention.

Before discussing some of the more relevant details of the system and method of the present invention, a brief overview of a mailpiece creation system employing an adhesive application and detection system will be provided. FIG. 1 depicts a schematic block diagram of a mailpiece creation system 10 according to the present invention wherein: (i) a supply of content material 212 is produced by a variety of upstream content fabrication modules 200, (ii) a wrapping system 300 receives a supply of wrapping material 412, i.e., from a plurality of wrapping material preparation modules 400, and (iii) a plurality of finishing modules 500 complete the mailpiece fabrication process including weighing, metering and printing postage indicia on each wrapped envelope.

Before the supply of wrapping material 412 is conveyed to the wrapping system 300, an adhesive application system 600 and adhesive detection system 100, according to the present invention, prepare the substrate material 414 for being wrapped/sealed around the content material 212. Furthermore, the operation of the mailpiece creation system 10 is coordinated, monitored and controlled by a system controller 50. While the entire mailpiece creation system 10 is described and illustrated as being controlled by a single system processor/controller 50, it should be appreciated that each of the modules 100-600 may be individually controlled by one or more processors. Hence, the system controller 50 may also be viewed being controlled by one or more individual microprocessors.

Upstream Content Fabrication Modules

In the described embodiment, the upstream content fabrication modules 200 include a feeder 210 containing a stack 214 of pre-printed sheets of content material 212. The pre-printed sheets of content material 212 are separated in the feeder 210 by a singulating apparatus 216 which uses a combination of guides 217, drive belts 218, and a stone roller 219 to retard the upper portion of the stack 212 while the lowermost sheet in the stack 212 is "singulated" or separated from the underside of the stack 212.

Next, the content material 212 is conveyed to a scanner 220 which reads information contained on select sheets of the content material 212 to provide mailpiece processing information to the controller 50. For example, a Beginning Of Collation (BOC) mark 222 may be read by a scanner 224 to indicate which sheet of content material 212, in a series of sheets being conveyed along a feed path FP, is the first sheet of a collation. These marks 222, also known as scan codes, are typically located in the margins of the content material 212 and are used to provide a myriad of information relating to the subsequent processing of the content material 212.

Scan codes 222 can provide information regarding whether a particular collation is to be folded, stitched, or stapled. Alternatively, a scan code can provide information regarding whether a particular mailpiece insert will be added to a particular sheet of content material 212 or to a collation of sheets of content material 212. Additionally, the scan code can provide information regarding the type of mailpiece being fabricated, i.e., whether the content material contains sensitive or confidential information. For example, some content material 212 may contain a recipient's social security number, credit card account information or private health information (protected under the HIPPA laws).

Once scanned, the sheets of content material 212 may then be grouped in an accumulator module 230 to produce a stacked collation of content material 212. A collation is typically produced by retarding the motion of select sheets in a pocket 232 of the accumulator module 230. Accordingly, the large stack of pre-printed sheets 212 which was singulated upstream by the feeder 210 may now be grouped together in smaller stacks to form one or more collations.

The content material 212, whether stacked into a collation or remaining as a single sheet, may be conveyed to a folding module 240 operative to fold the content material into a particular fold configuration. More specifically, the folding module 240 manipulates the content material around a plurality of press rollers 242 to produce various fold configurations, e.g., a bi-fold, C-fold, Z-fold or gate-fold configuration. Depending upon the processing information obtained from the scan codes 222, the fold module 240 may introduce a fold configuration into the content material 212 or pass the content material 212 unaffected to a chassis module 250.

The chassis module 250 performs one of the more important functions of the content fabrication modules 200 inasmuch a variety of additional information can be added to the content material 212 by way of mailpiece inserts 252, e.g., coupons, advertisements, solicitations, etc. Therein, a mailpiece insert 252 may be added by one of a series of overhead feeders 254a, 254b, 254c, 254f, 254e, 254f, and dropped onto a select piece of content material 212 as it passes beneath the overhead feeders 254a, 254b, 254c, 254f, 254e, 254f. Inasmuch as the system controller 50 knows the specific processing requirements and location of each piece of content material 212, i.e., location along the feed path, the overhead feeders 254a, 254b, 254c, 254f, 254e, 254f may selectively add inserts to build the content material 212 for a particular mailpiece recipient. For example, a specific advertisement, targeted to one mailpiece recipient, may be added by one of the feeders 254a, 254b, 254c, 254f, 254e, 254, while a coupon offering may be added to the content material 212 of another mailpiece recipient by another of the feeders 254a, 254b, 254c, 254f, 254e, 254f.

The content material 212 is then passed to a buffer module 270 through a right angle turn module (RAT) 260. Depending upon the space available for the various upstream content fabrication modules 200, the RAT 260 may, or may not, be required. The buffer module 270, on the other hand, performs another one of the more critical operations inasmuch as it serves as the "traffic manager" for the mailpiece creation system 10. More specifically, the buffer module 270 employs one (1) in-feed buffer gate G0 and five (5) buffer gates G1-G5 to coordinate the timing of the content material 212 from the chassis module 250 to the wrapping system 300. Such coordination is necessary to eliminate gaps or "dry-holes" when delivering content material 212 to the wrapping system 300.

In operation, the buffer module 270 receives input from the controller 50 regarding the flow of content material 212 from the chassis module 250 and determines the requisite speed of the wrapping system 300 to ensure that the supply of content material 212 is smooth and uninterrupted. Based upon the anticipated acceleration of the wrapping system 300, the controller invokes various algorithms to ensure that the wrapping system 300 is not exposed to accelerations which may rupture, tear or fail the supply of wrapping material 412. As a result reliability and throughput of the mailpiece creation system 10 is optimized.

In addition to optimizing throughput, the buffer module 270 ensures that content material 212 is properly "matched" with a supply of pre-printed wrapping material 312 and the resulting wrapped envelope contains the content material for which it was intended.

From the buffer module 270, the content material is passed to an input conveyor 280 at a right-angle for delivery to the wrapping system 300. The input conveyor 280 is conventional in its construction and includes pairs of drive fingers 282 which are driven by belts (also not shown) through elongate slots 284 in a transport deck 286. The drive fingers 282 engage a trailing edge of the content material 212 to convey the content material along the deck 285. To prevent the sudden impact of the fingers 282 from disrupting the registration of the content material 212, the input conveyor 280 includes a pair of drive rollers (not shown) to accelerate the content material 212 before being acted on by the drive fingers 282. That is, the drive rollers are operative to accelerate the content material 212 such that the drive fingers 282 engage the trailing edge at nearly the same speed as the content material 212. As such, a smooth transition occurs to prevent misalignment of the content material 212, e.g., a collation including one or more inserts, upon changing direction and velocity.

Several of the upstream content fabrication modules 200 have been designed and implemented for the first time as a result of being integrated with a mailpiece wrapping system 300 of the type described herein. Notwithstanding the longevity of service, upstream content fabrication modules of the type described herein are generally available from Pitney Bowes Inc., located in Stamford, Conn., a world-class leader in the manufacture of mailpiece inserters, sorters and mailpiece finishing equipment.

Mailpiece Envelope System

In FIG. 1, the wrapping system 300 receives content material from the input conveyor 280 while also receiving wrapping material 412 from the wrapping material preparation modules 400. With respect to the latter, prepared wrapping material 412 is fed to an upper conveyance deck 306 of the wrapping system 300 from a series of rollers 308 disposed beneath the deck 306. By "prepared" is meant that the wrapping material may have address or advertisement information pre-printed on a face of the wrapping material, be pre-cut to a particular envelope configuration, i.e., including windows for viewing internal information printed on the wrapped content material, and) have adhesive deposited in select areas.

The wrapping material 412 is drawn vertically upward (i.e., normal to the plane of the conveyance deck 306), across an upstream edge 310 of the deck 306 and horizontally downstream, i.e., in the direction of arrow FD, along the surface of the conveyance deck 306. As the wrapping material 412 is drawn over the upstream edge 310, the outboard edge portions 412O of the wrapping material 412 are pulled across a pair of guide rods 320 such that the outboard edge portions 412O converge at a point P and overlap. As such, the wrapping material 412 produces an "open-end" for accepting the content material 212 from the input conveyance 280. Furthermore, a tube-shaped wrap 412T is formed around the content material 212 as the wrapping material 412 is drawn together downstream of the open-end.

In the described embodiment, several pieces of content material 212 have been laid into the open end of the tube-shaped wrapping material 412T and spaced-apart by a pitch distance PI, i.e., the distance from the leading edge of one piece of content material 212a to the leading edge of the subsequent piece of content material 212b. Once wrapped, the tube-shaped wrapping material 412T is compressed by a triage of press rollers 330 to produce a strip 412S of sealed mailpiece envelopes. The strip 414S of sealed mailpiece envelopes is then is cut to produce individual wrapped envelopes 14 by a rotary cutter 336.

Wrapping Material Preparation Module (Adhesive application and Detection)

Figure 2:
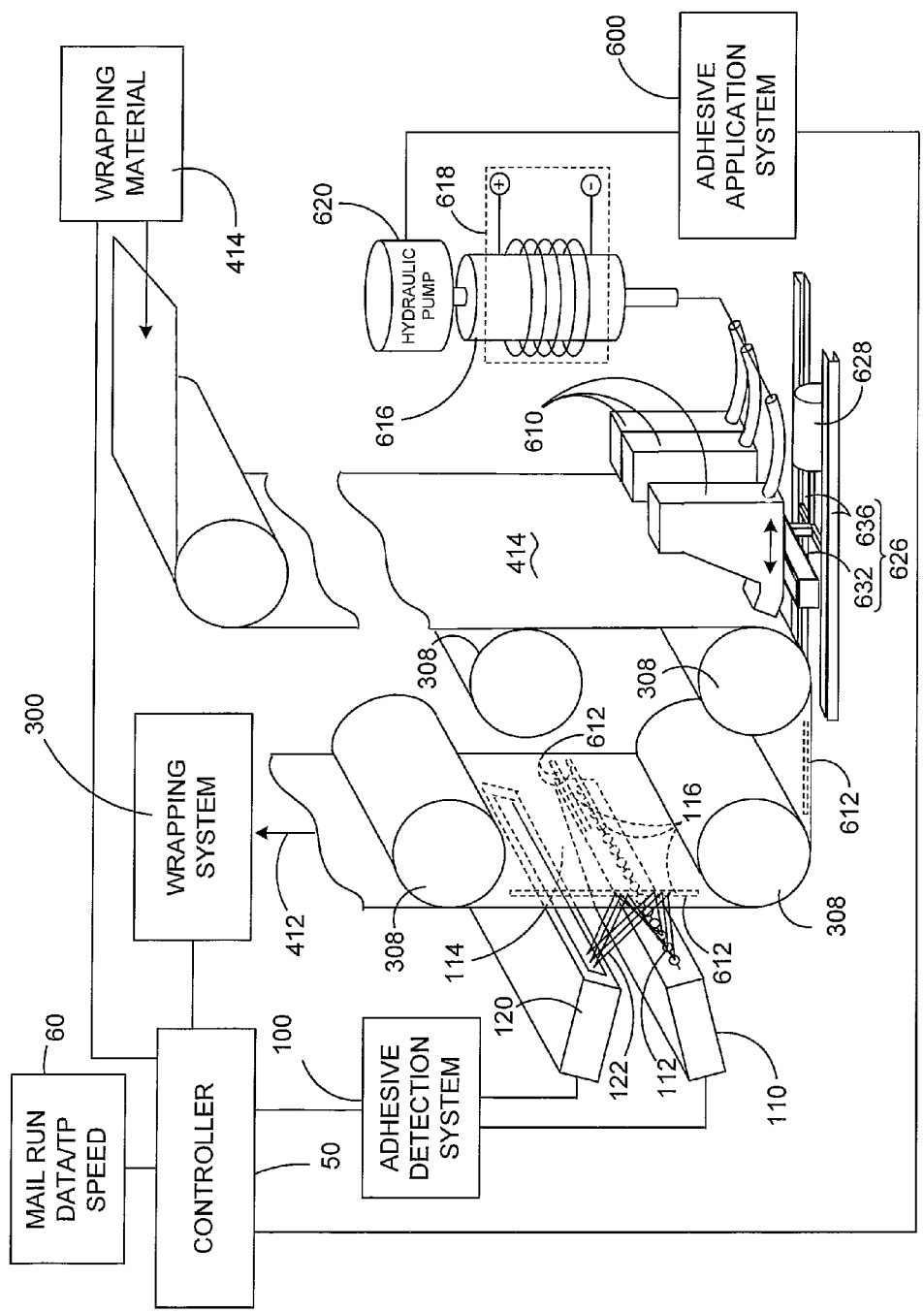
FIG. 2 is a broken-away perspective view of an adhesive application and detection system disposed on opposing surfaces of a mailpiece wrapping material.

In FIG. 2, the supply of wrapping material 412 is prepared as a flat-pattern substrate which is rolled into a web of substrate material 414. The flat pattern substrate may include pre-printed information such as recipient and sender address information (not shown) or may be pre-cut to include windows (also not shown) for viewing mailpiece address information printed on the content material.

In the described embodiment, the substrate material 414 is conveyed over a series of re-directing rollers 308 which direct the substrate material 414 downwardly passed an adhesive application system 600 and upwardly toward the deck 306 (see FIG. 1) of the wrapping system 300. The adhesive application system 600 includes a bank of application nozzles 610 for depositing a thin line/film of adhesive 612 on the substrate material 414 as it moves passed each of the nozzles 610. A supply of the adhesive 612 is contained in a pressure vessel 616 for feeding each of the application nozzles 610. The vessel 616 is heated to a temperature of about two hundred degrees Fahrenheit (200° F.) by a conventional electric heating element 618 and pressurized to an internal pressure of about between about thirty to ninety PSI (30-90 lb/in$^2$) by a hydraulic pump 620.

Additionally, the application nozzles 610 are mounted to a carriage assembly 626 which moves toward or away from the substrate material 414 by a linear actuator 628. More specifically, the application nozzles 610 are mounted to cross-member 632 bearing mounted to a pair of guide rails 636. Furthermore, the guide rails 636 are orthogonal to and disposed beneath the re-directing rollers 308.

Each time the wrapping system 300 demands a supply of wrapping material 412, the linear actuator 628 moves the bank of application nozzles 610 toward the substrate material 414 to deposit adhesive 612. The deposition of adhesive can be as straightforward as depositing a line of a predetermined thickness on the substrate material 414 as the substrate is conveyed across the head of each nozzles 610. Generally, the lines of adhesive 612 run parallel or orthogonal to the feed path FP of the substrate material 414. Gaps or breaks in the lines are predefined by the mail run data, i.e., the file containing mailpiece creation data, and made to effect a particular seal configuration when the wrapping material 414 is folded and cut by the wrapping system 300. Consequently, the gaps and breaks are fixed, i.e., the spacing therebetween is constant.

Notwithstanding the conventional manner for depositing adhesive 612, commonly owned, co-pending patent application entitled "Adaptive Adhesive application System", discloses an adhesive application system 100 which is variable to improve reliability and reduce the maintenance required in connection with the wrapping 300 and other modules 100-600. More specifically, the inventors discovered that by selectively controlling the nozzles 610, and the process for depositing the adhesive, cross-contamination of other modules, e.g., the rotary cutter 336, can be significantly reduced.

More specifically, the inventors discovered that under the typical pressures and flow rates demanded by the high throughput speed of the mailpiece creation system, it is difficult to prevent excess flow of adhesive when commanding the wrapping system 300 to suddenly stop or decelerate. Such a requirement to stop or suddenly decelerate may be caused by a tear in the wrapping material 414 or the requirement to re-sync the wrapping system 300 with the upstream content material fabrication modules 200.

The inventors discovered that by controlling the size of the nozzle aperture to decrease the flow of adhesive as a function of throughput/speed of the wrapping system 300, the difficulties associated with rapid deceleration of the wrapping system 300 are mitigated. While the specific function/algorithm can be found by reference to the co-pending application, it is suffice to say at this juncture that the deposition of adhesive by each of the application nozzles 610 varies as a function of throughput. While throughput is, at least initially, governed by the mail run data file 60, throughput may also be measured directly by monitoring the rotational speed of select encoders in the upstream content fabrication modules 200 or the speed of the mailpiece wrapping system 300.

Irrespective the requirement to control the flow of adhesive as described in the preceding paragraph, there is still a need to determine if the adhesive has been properly applied. For example, should the lack of adhesive prevent closure of the envelope, there is a chance that hundreds of envelopes 14 may be improperly sealed. While the lack of forming a proper enclosure may be relatively inconsequential for some envelopes 14, for others containing confidential information, e.g., a social security number, credit card number or bank account information, the legal liabilities can be significant for the mailer.

Accordingly, the present invention provides an adhesive detection system 100 which is reliable, yet does not add cost, change the chemical composition of the adhesive, or adversely impact the aesthetic appearance of the mailpiece. The inventor discovered that the inherent properties of the adhesive could be used to detect whether or not adhesive has been applied to the substrate material 414. More specifically, the inventor discovered that the physical properties of commonly used polymer adhesives, such as polyolefin, polyamides, ethyl vinyl acetates, and polyurethanes due to the conjugation of double bonds, could be used to detect whether or not the adhesive was applied. Additionally UV stabilizers can also be added to the polymer to increase ultraviolet EM absorption.

Figure 3:
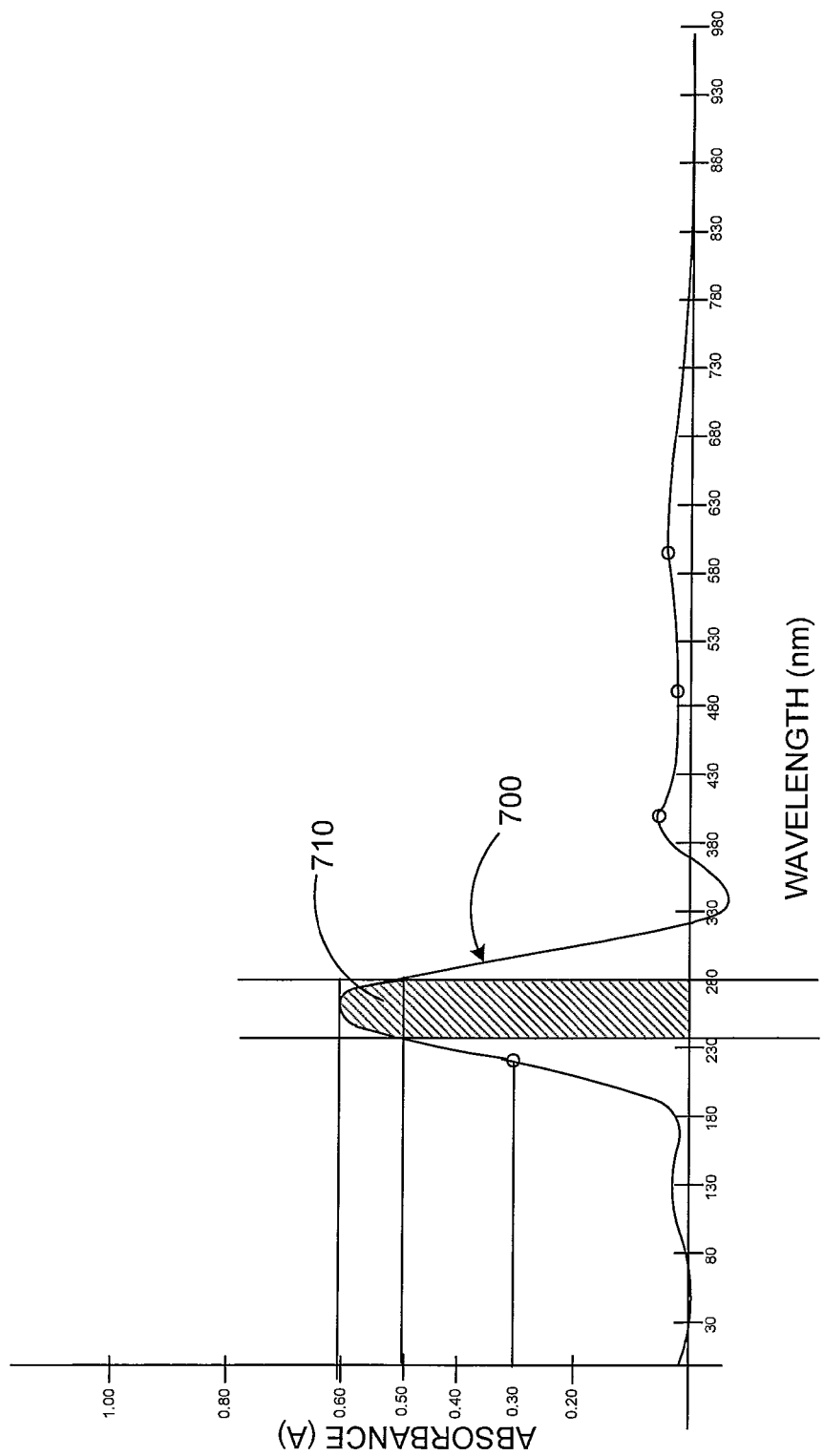
FIG. 3 is a graphical depiction of the absorbance of a polymer adhesive as a function of wavelength from zero to one-thousand nanometers (0 nm-1000 nm) in wavelength.

In FIGS. 2 and 3, a system 100 for detecting adhesive deposited on the substrate material 414 is disposed immediately downstream of the adhesive application system 600. The system 100 comprises a source 110 of ElectroMagnetic (EM) energy 112, in at least the short UV range, to illuminate the surface 114 of the substrate material 414, i.e., select regions 116 where the adhesive 612 is anticipated to be deposited. A source of EM energy 112 suitable for irradiating the surface 114 with UV light may be a short UV Light Emitting Diode (LED) or series short UV LEDs. Furthermore, a fluorescent UVC germicidal lamp may be used to illuminate the substrate 414. Any known illumination can be used, such as, UV lasers, as long as they emit EM energy in the short UV range. By "short UV" range means between one-hundred (100 nm) to about three-hundred nanometers (300 nm). Preferably still, a short UV range means between two-hundred forty nanometers (240 nm) to about two-hundred eighty nanometers (280 nm).

The wrapping material or substrate 414 is a conventional fiber reinforced, resin impregnated white paper which, when irradiated with short UVC energy, emits or fluoresces EM energy in the visible light range (i.e., a higher wavelength) of between about four-hundred nanometers (400 nm) to eight hundred nanometers (800 nm). While the wrapping material 414 emits energy in the visible light range when irradiated with short UVC energy, the polymeric adhesive 612 absorbs the most or all of the UVC energy. Consequently, the polymeric adhesive 612 can be viewed as blocking the UV energy from reaching the underlying substrate material 414.

Additionally, the system 100 includes an EM energy detection device 120 operative to detect energy 122 reflected from the surface 114 of the substrate material 414 in the visible light range of between about four-hundred nanometers (400 nm) to eight hundred nanometers (800 nm). An EM detection device 120 suitable for practicing the invention includes a light-to-voltage sensor used to collect the light emitted from the substrate 414 and convert the light to an analog voltage. Any other energy detection methods can be used such as, a photocathode or a CCD/Vision system.

FIG. 3 depicts a graph 700 of the optical absorbance of the polymer adhesive 612, i.e., the response detected by the EM detection device 120, as a function of wavelength. The cross-hatched area 710 under curve reveals the absorbance of the polymeric adhesive 612 in the short UV range. In the described embodiment, the amplitude of the response reaches a maximum value of about 0.6 on a scale of energy absorbance with an adhesive film thickness of 0.05 mm using a Perkin Elmer Lambda 900 Spectrophotometer.

The system controller 50, or a processor dedicated to the adhesive detection system 100, is operative to analyze the response of the EM energy detection device 120. The detection system 120 determines when the EM energy 700 emitted is below a threshold level signaling the absorbance of energy by the adhesive 612. The threshold level will generally be determined by a calibration step at system start-up, however, in the described embodiment, a threshold level of about 0.5 may be suitable for detecting the presence of adhesive on the substrate material 414.

To facilitate detection, optical brighteners are often incorporated, or can be added, into the substrate material 414 such that the combined effect augments the effectiveness of the adhesive detection system 100. More specifically, such brighteners increase the signal that the EM detection device 120 receives. The Perkin Elmer Lambda 900, is equipped with an integrating sphere to collect all light from the sample.

When employing a light-to-voltage sensor as the EM detection device 120 an input band-pass filter may be employed to improve the signal-to-noise ratio. More specifically, a band-pass filter enabling the passage of a narrow band of blue light at about 430 nanometers may be used to improve the signal. Alternatively, the lens of the detection device may be coated with a blue dye to produce the same effect.

While the adhesive detection system 100 of the present invention shows the source of EM energy 110 and EM detection device 120 as separate elements, it will be appreciate that the source and detection devices 110, 120 may be a single integrated unit. Furthermore, while the adhesive detection system 100 is shown as being on a side opposite to the adhesive application system 600, it will be appreciated that the detection and application systems 100, 600 may be on the same side of the substrate material 414, or at right-angles relative to each other depending upon the arrangement of the re-direct rollers 308.

Figure 4:
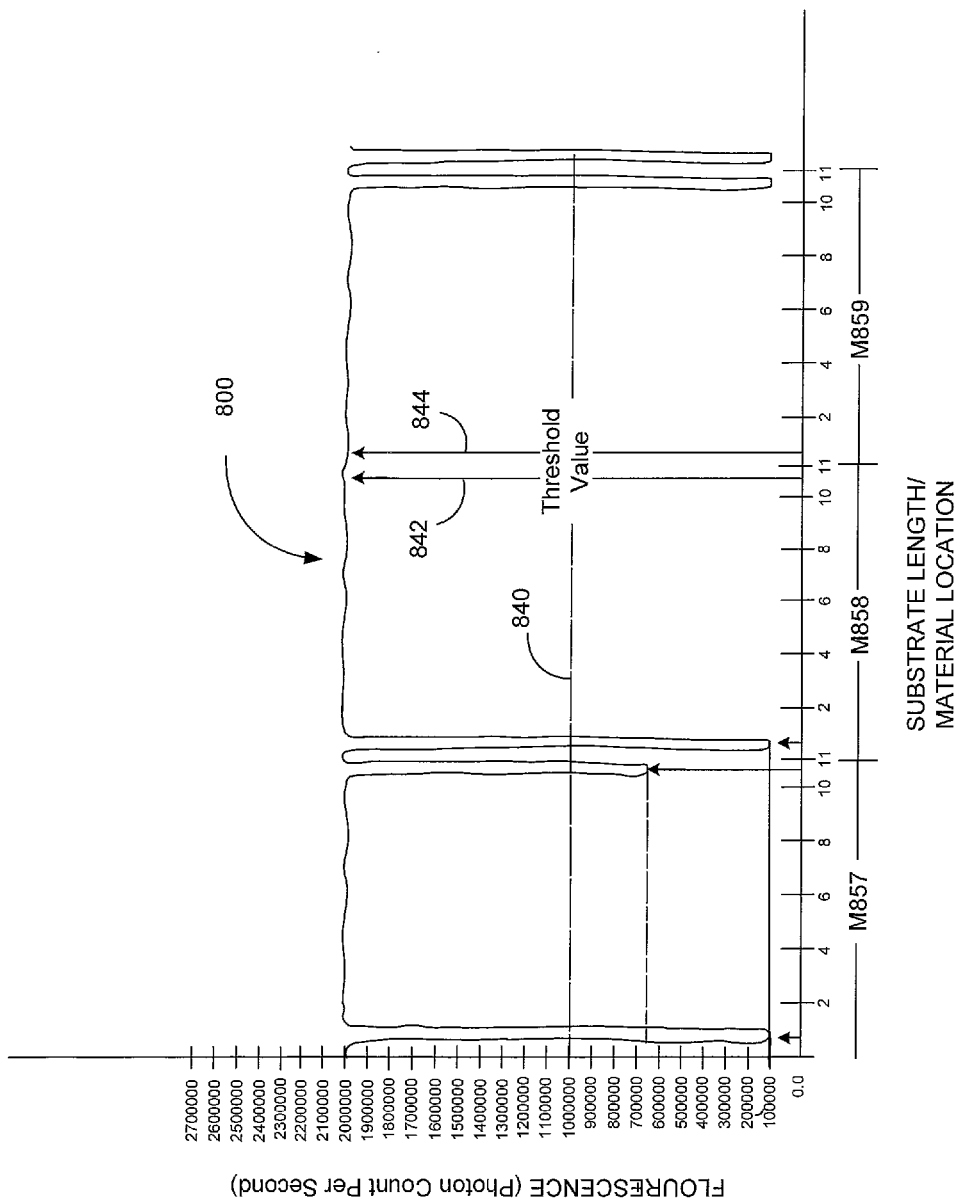
FIG. 4 is a graphical depiction of the absorbance of the polymer adhesive in combination with a substrate material as a function of wavelength from zero to one-thousand nanometers (0 nm-1000 nm) in wavelength.

FIG. 4 depicts a graph 800 of the EM energy 810 emitted or fluorescing from the surface 114 of the substrate material 414 in the visible light range as a function of material position/length paid-out from the supply 412. More specifically, the EM energy emitted 810 is shown for a particular length of material 414 corresponding to mailpieces 857, 858 and 859.

Therein, it will be appreciated that the EM energy reflected from the surface of the wrapping material 412, is measured in the number of photons received per second. In the described embodiment, the surface 412 emits about $2\times10^6$ photons/sec. Upon encountering a strip of adhesive 612 on the surface 412, the number of photons emitted drops substantially to only about $1.0\times10^5$. In the described embodiment, a threshold value, of $5.0\times10^5$ (see the horizontal line 840 has been established as a level that, if the detected value is below, then an adhesive 612 is present. In this example, the EM detection device 120 receives electromagnetic energy in areas where adhesive was anticipated but not detected. That is, in areas corresponding to mailpieces 858 and 859, stations 10.5 and 0.5, respectively, the level of electromagnetic energy detected far exceeded the threshold value, hence no adhesive was detected. Additionally, in the area corresponding to mailpiece 857, the electromagnetic energy detected was below the threshold value of $1.0\times10^6$, but not significantly below, i.e., at about $6.5\times10^5$. While this value may be "less than the threshold value", it may be indicative of other problems yet to be seen or resolved.

Having determined by the controller 50 that, at least envelopes 858 and 859, have been improperly wrapped, in some way which is yet to be determined, the controller 50 issues a cue or signal, that envelopes 858 and 859 are out-sorted in an out-sort module 180 downstream of the wrapping system 300. Other mailpieces such as mailpiece 857 which meet the criteria but are within a threshold range of values, e.g., between $6.0\times10^5$ and $1.4\times10^6$, may be flagged for visual or other form of inspection.

Finishing Modules

Once the individual wrapped envelopes 14 are cut, the mailpieces are completed by a series of finishing modules 500. The finishing modules may, inter alia, include a scale 510, a meter 520, a printer 520 and a tray or bin 530 for collecting the mailpieces. The scale 510 determines the weight of each mailpiece, but may also include a scanner to determine the size/volume of the mailpiece. Once the size/weight of the mailpiece has been determined a postage meter determines the postage required for delivery of the mailpiece. The printer 530 applies the postage indicia to the mailpiece and any other mailpiece information which may be required, e.g., destination and/or return address information. Finally, the mailpieces may be accumulated in a tray or bin for ease of delivery.

It is to be understood that all of the present figures, and the accompanying narrative discussions of preferred embodiments, do not purport to be completely rigorous treatments of the methods and systems under consideration. For example, while the invention describes an interval of time for completing a phase of sorting operations, it should be appreciated that the processing time may differ. A person skilled in the art will understand that the steps of the present application represent general cause-and-effect relationships that do not exclude intermediate interactions of various types, and will further understand that the various structures and mechanisms described in this application can be implemented by a variety of different combinations of hardware and software, methods of escorting and storing individual mailpieces and in various configurations which need not be further elaborated herein.

The invention claimed is:

1. A system for detecting adhesive deposited on a substrate material comprising:
    a source of ElectroMagnetic (EM) energy in at least the short UV range to illuminate a surface of the substrate material anticipated to have an adhesive deposited thereon in select regions;
    an EM energy detection device operative to detect energy reflected from the surface of the substrate material in the visible light range and produce a response indicative of the optical absorbance of EM energy in the short UV range; and
    a processor operative to analyze the response of the EM energy detection device to determine whether light energy in the visible range is below a threshold level to indicate the presence of adhesive deposited on the substrate material.

2. The system according to claim 1 wherein the short UV is within a range of about 240 nanometers to about 280 nanometers in wavelength.

3. The system according to claim 1 wherein the threshold level of absorbance is in the short UV range and greater than about 0.3.

4. The system according to claim 3 wherein the threshold level of absorbance is in the short UV range and greater than about 0.5.

5. The system according to claim 1 wherein the source of ElectroMagnetic (EM) energy is at least one short UV Light Emitting Diode (LED).

6. The system according to claim 1 wherein the source of ElectroMagnetic (EM) energy is a fluorescent UVC germicidal lamp.

7. The system according to claim 1 wherein the EM energy detection device is a light-to-voltage sensor.

8. The system according to claim 7 wherein the light-to-voltage sensor includes an input band-pass filter enabling the detection of a narrow band of energy at about 430 nanometers in wavelength.

9. The system according to claim 8 wherein the light-to-voltage sensor includes an input lens having a resin coating thereon, the resin coating mixed with a blue dye.

10. A method for detecting adhesive deposited on a substrate material comprising:
    illuminating a surface of the substrate material with electromagnetic energy in at least the short UV range; detecting EM energy reflected from the surface of the substrate material and producing a response due to the optical absorbance of EM energy in at least the short UV range, and evaluating the energy reflected from the substrate material as a function of the location along the strip of substrate material to analyze the fluorescence in areas corresponding to areas where adhesive is anticipated; providing a cue when absorbance of EM energy is below a threshold level.

11. The method according to claim 10 further including the steps of: finishing the envelopes such that each is suitable for delivery, and out-sorting envelopes upon the receipt of the cue.

12. The method according to claim 10 further including the step of: band-pass filtering EM energy to enable the detection of a narrow band of EM energy fluorescing from the substrate material.

* * * * *